(12) United States Patent
Juels

(10) Patent No.: US 10,230,699 B2
(45) Date of Patent: Mar. 12, 2019

(54) PRIVACY-PROTECTING SYSTEM AND METHOD FOR WIRELESS MEDICAL DEVICES

(71) Applicant: PCMS Holdings, Inc., Wilmington, DE (US)

(72) Inventor: Ari Juels, New York, NY (US)

(73) Assignee: PCMS Holdings, Inc., Wilmington, DE (US)

( * ) Notice: Subject to any disclaimer, the term of this patent is extended or adjusted under 35 U.S.C. 154(b) by 0 days.

(21) Appl. No.: 15/739,638

(22) PCT Filed: Jun. 28, 2016

(86) PCT No.: PCT/US2016/039878
§ 371 (c)(1),
(2) Date: Dec. 22, 2017

(87) PCT Pub. No.: WO2017/007642
PCT Pub. Date: Jan. 12, 2017

(65) Prior Publication Data
US 2018/0191693 A1 Jul. 5, 2018

Related U.S. Application Data

(60) Provisional application No. 62/189,042, filed on Jul. 6, 2015.

(51) Int. Cl.
*H04M 1/66* (2006.01)
*H04L 29/06* (2006.01)
(Continued)

(52) U.S. Cl.
CPC ........ *H04L 63/0492* (2013.01); *A61B 5/0031* (2013.01); *A61N 1/37252* (2013.01);
(Continued)

(58) Field of Classification Search
USPC ..................................................... 340/573.1
See application file for complete search history.

(56) References Cited

U.S. PATENT DOCUMENTS 9,402,545 B2 * 8/2016 Baker .................. H04W 76/38
2005/0241026 A1 * 10/2005 Esler .................. A61N 1/37258
705/2

(Continued)

OTHER PUBLICATIONS

Notification of transmittal of the International Search Report and the Written Opinion of the international Searching Authority, or Declaration for PCT/US2016/039878 dated Sep. 9, 2016. 13 pages.
(Continued)

*Primary Examiner* — David Q Nguyen
(74) *Attorney, Agent, or Firm* — Invention Mine LLC

(57) ABSTRACT

Systems and methods are provided for protecting the privacy of wireless enabled medical device (WEMD) communications, particularly against traffic-analysis attacks. In an exemplary method, a WEMD measures a physiological parameter and conveys that physiological parameter to a WEMD-receiver using messages that simulate at least one message from a cover device, for example by embedding physiological data in a message from a simulated cover device. In some embodiments, the WEMD sends messages that simulate traffic patterns of the cover device. The cover device may be a device not associated with serious medical conditions, such as a fitness-oriented heart rate monitor. In some embodiments, the simulation is discontinued under emergency conditions or in particular regions that are deemed to be safe.

16 Claims, 6 Drawing Sheets

(51) Int. Cl.
| | |
|---|---|
| *A61B 5/00* | (2006.01) |
| *A61N 1/372* | (2006.01) |
| *G06F 19/00* | (2018.01) |
| *H04L 12/00* | (2006.01) |
| *H04L 12/64* | (2006.01) |
| *H04W 12/02* | (2009.01) |
| *G16H 40/63* | (2018.01) |
| *G16H 10/65* | (2018.01) |
| *H04W 84/18* | (2009.01) |
| *H04W 12/08* | (2009.01) |
| *H04W 12/10* | (2009.01) |

(52) U.S. Cl.
CPC ......... *A61N 1/37254* (2017.08); *G06F 19/00* (2013.01); *G06F 19/3418* (2013.01); *G16H 10/65* (2018.01); *G16H 40/63* (2018.01); *H04L 12/00* (2013.01); *H04L 12/6418* (2013.01); *H04W 12/02* (2013.01); *H04W 12/08* (2013.01); *H04W 12/10* (2013.01); *H04W 84/18* (2013.01)

(56) References Cited

U.S. PATENT DOCUMENTS

| | | | |
|---|---|---|---|
| 2007/0255116 A1 | 11/2007 | Mehta | |
| 2009/0043355 A1* | 2/2009 | Cazares | A61B 5/0031 607/32 |
| 2011/0006876 A1* | 1/2011 | Moberg | G06F 19/3418 340/3.2 |
| 2013/0211651 A1* | 8/2013 | Schaible | F16M 11/20 701/22 |
| 2014/0180366 A1* | 6/2014 | Edlund | A61N 1/3622 607/60 |
| 2015/0089590 A1 | 3/2015 | Krishnan | |
| 2015/0123800 A1* | 5/2015 | Montague | A61B 5/742 340/573.1 |
| 2016/0135706 A1* | 5/2016 | Sullivan | A61B 5/0059 600/301 |
| 2017/0372600 A1* | 12/2017 | Palin | G06F 3/0484 |
| 2018/0011988 A1* | 1/2018 | Ziegler | G06F 19/3468 |

OTHER PUBLICATIONS

Zhang Meng et al: "Trustworthiness of Medical Devices and Body Area Network", Proceedings of the IEEE, IEEE. New York, US, vol. 102, No. 8, Aug. 1, 2014 (Aug. 1, 2014 ), pp. 1174-1188, XP011553685, ISSN: 0018-921, DOI: 10.1109/JPROC.2014. 2322103 [retrieved on Jul. 18, 2014] the whole document. 15 pages.

Shuai Li et al: "Facet: Streaming over Videoconferencing for Censorship Circumvention", Privacy in the Electronic Society, ACM, 2 Penn Plaza, Suite 701 New York NY 10121-0701 USA, Nov. 3, 2014 (Nov. 3, 2014), pp. 163-172, XP0580061325, DOI: 10.1145/26659431665944 ISBN: 978-1-4503-3148-7 the whole document. 10 pages.

R. Rekha et al: "Secure Medical Data Transmission in Body Area Sensor Networks Using Dynamic Biometrics and Steganography", Bonfring International Journal of Software Engineering and Soft Computing, Mar. 1, 2012 (Mar. 1, 2012), pp. 5-11, XP055298906, Retrieved from the Internet: URL:http://www.journal.bonfring.org/papers/sesc/volume2/BIJ-002-1125.pdf [retrieved on Aug. 31, 2016] the whole document. 7 pages.

Notification of transmittal of the international preliminary report on patentability, for PCT/US2016/039878 dated Jun. 29, 2017, 15 pages.

Daniel Halperin, et al., "Pacemakers and Implantable Cardiac Defibrillators: Software Radio Attacks and Zero-Power Defenses". In IEEE Symposium on Security and Privacy, 2008.

K. P. Dyer, S.E. Coull, T. Ristenpart, and T. Shrimpton. Protocol misidentification made easy with format-transforming encryption. In ACM SIGSAC Conference on Computer & Communications Security, 2013.

W. Burleson, S. S. Clark, B. Ransford, and K. Fu. Design challenges for secure implantable medical devices. In Design Automation Conference, pp. 12-17, 2012.

A. Hintz. Fingerprinting websites using traffic analysis. In R. Dingledine and P. Syverson, editors, Proceedings of the Privacy Enhancing Technologies workshop, 2002.

M. Rushanan, A. D. Rubin, D. F., Kune, and C. M. Swanson, C. M. SoK: Security and privacy in implantable medical levices and body area networks. In IEEE Security and Privacy (SP), pp. 524-539, 2014.

A. Houmansadr, C. Brubaker, and V. Shmatikov, The parrot is dead: Observing unobservable network communications. In IEEE Security and Privacy (SP), pp. 65-79, 2013.

D. Wagner and P. Soto. Mimicry attacks on host-based intrusion detection systems. In ACM Conference on Computer and Communications Security, 2002.

B. Defend, et. al., "Protecting Global Medical Telemetry Infrastructure", University of Massachusetts Amherst and Kyushu University, Trustees of Dartmouth College, Jan. 7, 2008.

L. Buttyan and T. Holczer, "Traffic Analysis Attacks and Countermeasures in Wireless Body Area Sensor Networks". Laboratory of Cryptography and Systems Security (CrySyS). Budapest University of Technology and Economics, 978-1-4673-1239-4, IEEE 2012.

N. Ellouze, et. al. "Digital Investigation of Security Attacks on Cardiac Implantable Medical Devices", pp. 15-30, Oct. 2014.

* cited by examiner

PRIVACY-PROTECTING SYSTEM AND METHOD FOR WIRELESS MEDICAL DEVICES

CROSS-REFERENCE TO RELATED APPLICATIONS

This application is a national stage application under 35 U.S.C. 371 of International Application No. PCT/US2016/039878, entitled "PRIVACY-PROTECTING SYSTEM AND METHOD FOR WIRELESS MEDICAL DEVICES", filed on Jun. 28, 2016, which claims priority to and the benefit under 35 U.S.C. § 119(e) of U.S. Provisional Patent Application Ser. No. 62/189,042, filed Jul. 6, 2015, titled "PRIVACY-PROTECTING SYSTEM AND METHOD FOR WIRELESS MEDICAL DEVICES", which is hereby incorporated in its entirety by reference.

BACKGROUND

Wirelessly enabled medical devices (WEMDs) are electronic instruments carried by patients to monitor and/or treat medical conditions. One common variety, known as an implantable medical device (IMD), is a WEMD that is surgically inserted either partially or fully into a patient's body. WEMDs provide monitoring and automatic therapies to help treat a wide range of chronic medical disorders. They are often fully instrumented embedded computing devices, with CPUs, sensors, actuators, and bi-directional radios. IMDs in particular are in use by millions of patients worldwide, and their applications and base of users are rapidly growing.

Technologists anticipate that advances in power management, wireless communication, and computation will enable WEMDs to communicate wirelessly with consumer devices such as mobile phones and smartwatches and also intercommunicate through body area networks (BANs) in order to orchestrate monitoring and therapies across different organs. Such communications, however, will be vulnerable to eavesdropping and other manipulation. Today, over-the-air attacks against IMDs have already been documented that may seriously infringe patient privacy and potentially be fatal. Encryption and cryptographic integrity protection are the most prevalent solution to such attacks. However, those countermeasures are not entirely successful against all types of attack. For example, encryption may largely conceal the content of wireless communications. But an adversary may still potentially discover the presence of a particular medical device on or in a patient's body and learn information about its communications through traffic analysis by studying the sizes and timing of encrypted messages. Thus, encryption may fail to conceal certain highly sensitive information about a user's medical status.

Standard cryptographic techniques such as authenticated encryption may protect the integrity and secrecy of WEMDs communications against eavesdroppers. WEMDs may also attempt to conceal their presence by not transmitting any device identifiers in the clear. Nonetheless, the presence of specific WEMD types may be discovered by traffic analysis through analysis of message sizes and patterns of device communication.

A WEMD (e.g., a deep brain stimulator) may transmit information about a person's medical condition (e.g., that she has a serious neurological disorder). Such information may be used to discriminate against a victim (e.g., in employment decisions), to target the victim for physical attack (e.g., exploit weaknesses in the IMD of a high-profile user), or to create nuisances such as targeted advertising (e.g., for medications suitable for a victim's medical condition). Additionally, traffic analysis may indicate information about the content of WEMD communications. For example, if an implanted cardioverter defibrillator (ICD) transmits a signal only when the ICD performs a therapy process related to a patient's heart, the mere presence of a signal may indicate a cardiac event. Thus, traffic analysis poses a threat to patient privacy that cryptography, a common tool for communications security, fails to address. Countermeasures to traffic analysis have been proposed in certain domains, such as censorship evasion, as described in K. P. Dyer, S. E. Coull, T. Ristenpart, and T. Shrimpton, *Protocol Misidentification Made Easy with Format-Transforming Encryption*. ACM SIGSAC Conference on Computer & Communications Security, 61-72 (2013), and Shuai Li, Mike Schliep, and Nick Hopper. *Facet: Streaming Over Videoconferencing for Censorship Circumvention*. ACM Workshop on Privacy in the Electronic Society, 163-172 (2014). Countermeasures to traffic analysis have further been proposed for the purposes of attacking intrusion-detection systems (IDSs), as described in D. Wagner and P. Soto, *Mimicry attacks on host-based intrusion detection systems*. ACM Conference on Computer and Communications Security, 255-264 (2002).

Consumers care about the privacy of medical information, particularly when such privacy relates to devices carried on or near the body. The security of IMDs in particular has been a hot-button topic because of life-threatening attacks demonstrated by researchers and the high-profile decision by former Vice President Dick Cheney to have the wireless interface on his IMD deactivated—at great inconvenience—due to security concerns.

SUMMARY

The systems and methods described herein conceal use of a wireless-enabled medical device (WEMD) by detecting nearby devices, selecting a cover device, measuring physiological data applicable to the user, and simulating the cover device to transmit the physiological parameter data. The cover device may be selected to be different from any detected nearby device, and the user, optionally, may perform the selection. Simulating the cover device may include sending messages with packet lengths and timings associated with the selected device. Simulation of a cover device may be ceased in an emergency or upon entering a safety zone. Such methods and systems help to protect patient privacy and prevent traffic-analysis attacks on encrypted medical device communications by mimicking transmissions of different device types.

DETAILED DESCRIPTION

The systems and methods disclosed herein operate to protect WEMD traffic privacy using the technique of device mimicry. In exemplary embodiments, communications of a WEMD are embedded within traffic plausibly generated by a different device type, which may be a non-medical device (e.g., a smartwatch with a fitness application) or a medical device associated with a different medical status than a patient's true one. The mimicked device may use the same wireless communication protocol (MAC and PHY) as the WEMD. For example, if the WEMD communicates via Bluetooth LE, a device capable of communicating via Bluetooth LE is selected to be mimicked.

In the present specification, a (trusted) device communicating with the WEMD is referred to as a WEMD-receiver (or simply receiver). A simulated (non-medical) device is referred to herein as a cover device, and its traffic is referred to as cover traffic. A device that normally communicates with the cover device is referred to herein as a cover-device receiver or cover-receiver. The cover device is preferably selected such that the cover-device and cover-receiver communicate over an encrypted (and authenticated) channel.

Encryption fails to address the risk of traffic analysis against WEMD communications. Systems and methods are described herein for protocol mimicry that are specific to WEMDs. For example, some embodiments generate cover traffic using real physiological measurements, provide an emergency-traffic override, or enable designation of safety zones.

Figure 1:
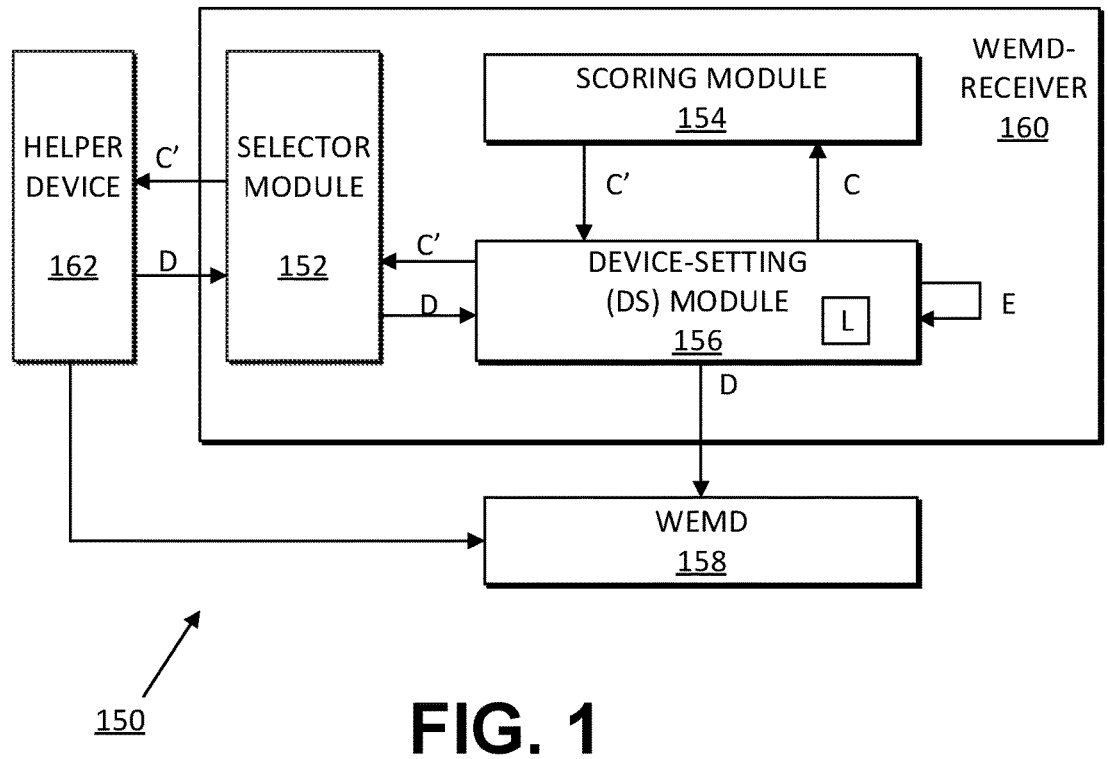
FIG. 1 is a functional block diagram illustrating exemplary components used in an embodiment of a privacy-protecting system.

FIG. 1 depicts an architecture block diagram with message flows. FIG. 1 illustrates message flows used for device setting by a WEMD-receiver 160 in some embodiments. The receiver 160 stores a list of device types capable of being mimicked. The receiver 160 may further detect device types in the neighborhood of the receiver. The detected device types may be eliminated as potential choices for a cover device. The receiver's scoring module 154 scores the remaining potential cover device choices. The scoring module 154 may consider device type parameters, such as transmission protocols and physiological measurement data type, in calculating a score for each potential cover device type. The selector module 152 selects a cover device D. The selector module 152 stores the selection D in memory. Selector module 152 may use the potential cover device scores in determining which cover device type to mimic. A device-setting module 156 stores a selected cover device D and communicates D to a WEMD 158. For one embodiment, a device-setting module 156 is included in a receiver device 160, which is part of a wireless enabled medical device (WEMD) system 150.

In some embodiments, selection of a device type to be mimicked is made by a helper device that is paired with one or both of a WEMD 158 and a receiver 160. For example, the WEMD 158 may be an implantable medical device (IMD), the receiver 160 a smartwatch, and the helper 162 a smartphone. In such embodiments, a helper device 162 may transmit a choice of D to both a WEMD 158 and a receiver 160. In another embodiment, cover device selection is made by a WEMD 158, in which case a WEMD 158 communicates D to a receiver 160. Once a cover device D has been selected, a WEMD 158 and a receiver 160 are prepared to mimic the mutually agreed-upon cover device using a protocol described below.

In an exemplary embodiment, a receiver 160 is paired with a WEMD 158 using a standard protocol (e.g., Bluetooth pairing), and a receiver 160 is pre-populated with a predetermined list L of available cover-device types that a receiver 160 is capable of using for cover traffic. This list may be embedded in software or hardware on a WEMD-receiver 160 and/or may be received through a remote transmission or update.

In an exemplary embodiment, a method is performed for selection of a cover-device and cover-device receiver. Cover-device selection may be performed by a device-setting (DS) module 156 in a receiver 160.

In an exemplary embodiment, for cover device selection, a DS module 156 scans and constructs a list E of device types in the neighborhood that represent potential cover-device types of which a user typically carries only one. The residual list of potential cover devices C is list L minus the device types on list E.

In an exemplary embodiment, for cover-device scoring, the DS module 156 uses a scoring module 154 to score available cover device types on list C based on at least in part on a calculated utility function (e.g., weighted sum) computed for the features of the plurality of available cover device types, such as bandwidth, privacy strength, and power consumption, as stored in L. The scoring module 154 may rank potential devices according to their scores. The scoring module 154 may return a scored (and optionally ranked) list C'.

In an exemplary embodiment, for cover-device selection, the DS module 156 uses a selector module 152 to choose a cover-device type D from C'. If a receiver 160 has a user interface, e.g., via a smartphone application, a selector module 152 may enable selection by the user, e.g., through presentation of a menu of options in C'. Optionally, the user may have the opportunity to mark as spurious, devices in E that are not carried by the user (e.g., nearby devices that do not belong to or are not regularity carried by the user). A selector module 152 may present device candidate rankings to the user, for example, in decreasing order of ranking. Alternatively, a selector module 152 may make a selection automatically. In one embodiment, a selector module 152 may set D to the top-ranked device in C'.

For cover-device instantiation, a DS module 156 may locally set D as a cover-device type for its communication with a WEMD 158. A receiver 160 transmits D to a WEMD 158, which similarly sets D as its cover-device type.

In an optional adaptation step, a DS module 156 performs periodic polling to determine whether there have been changes in list E. If there have been changes, a DS module 156 may return to cover-device selection.

Figure 2:
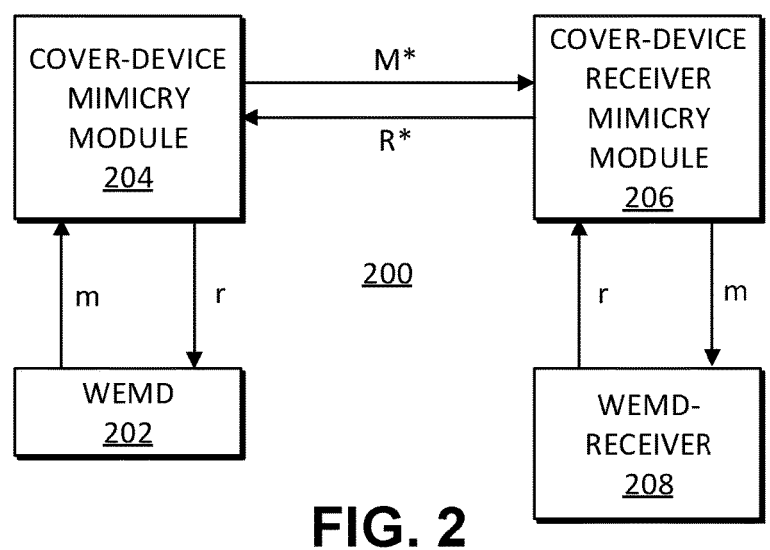
FIG. 2 is a functional block diagram of an exemplary embodiment in which a WEMD and WEMD-receiver send messages through respective mimicry modules.

FIG. 2 is a general block diagram depicting an exemplary system 200. In the embodiment of FIG. 2, WEMD 202 transmits message m to a WEMD-receiver 208 by way of a simulated (or in some embodiments, fully emulated) cover-device 204/cover-device receiver 206 pair. A message m is incorporated into a message M* and transmitted by a cover-device mimicry module 204, which may be co-located with a WEMD 202. M* is received by a cover-device receiver mimicry module 206, which extracts underlying message m and passes message m to a WEMD-receiver 208. Analogously, transmission of a message r proceeds from a WEMD-receiver 208 to a WEMD 202.

Symbols m and r denote messages sent by the WEMD 202 and receiver 208, respectively, and M* and R* denote messages sent, respectively, by the cover-device mimicry module 204 and cover-device receiver mimicry module 206. For clarity, this specification omits subscripts, and operations are described with respect to individual messages. All devices, real and simulated, however, transmit sequences of messages (e.g., $m_1$, $m_2$, . . . ) and communicate asynchronously, and that the operations described may be applied to message sequences. For example, a WEMD message m may be embedded across multiple cover-device messages.

A possibility exists for eavesdropping on transmissions during a selection process. As this selection process protocol is performed only rarely, however, such eavesdropping is of limited concern. In some embodiments, cover traffic is also generated for a selection process. A WEMD 202 and receiver 208 use, respectively, a cover-device mimicry module 204 and a cover-device receiver mimicry module 206. In one embodiment, these modules are connected to their respective devices (WEMD 202 and receiver 208) by a wired interface such that module-to-device transmissions are not vulnerable to eavesdropping. Alternatively, a module-to-device channel may rely on a wireless transmission protocol that itself is a form of cover traffic or which an adversary is unable to detect. For example, pulse-based ultra-wideband (UWB) emissions may be made difficult for an adversary to detect.

An eavesdropper on wireless transmissions transmitted using embodiments described above will receive traffic that is statistically similar to or identical to that transmitted by a legitimate cover device. An adversary will be unable to detect the presence of a WEMD 202/WEMD-receiver 208 pair or determine information from a WEMD 202 using a side channel.

Figure 3:
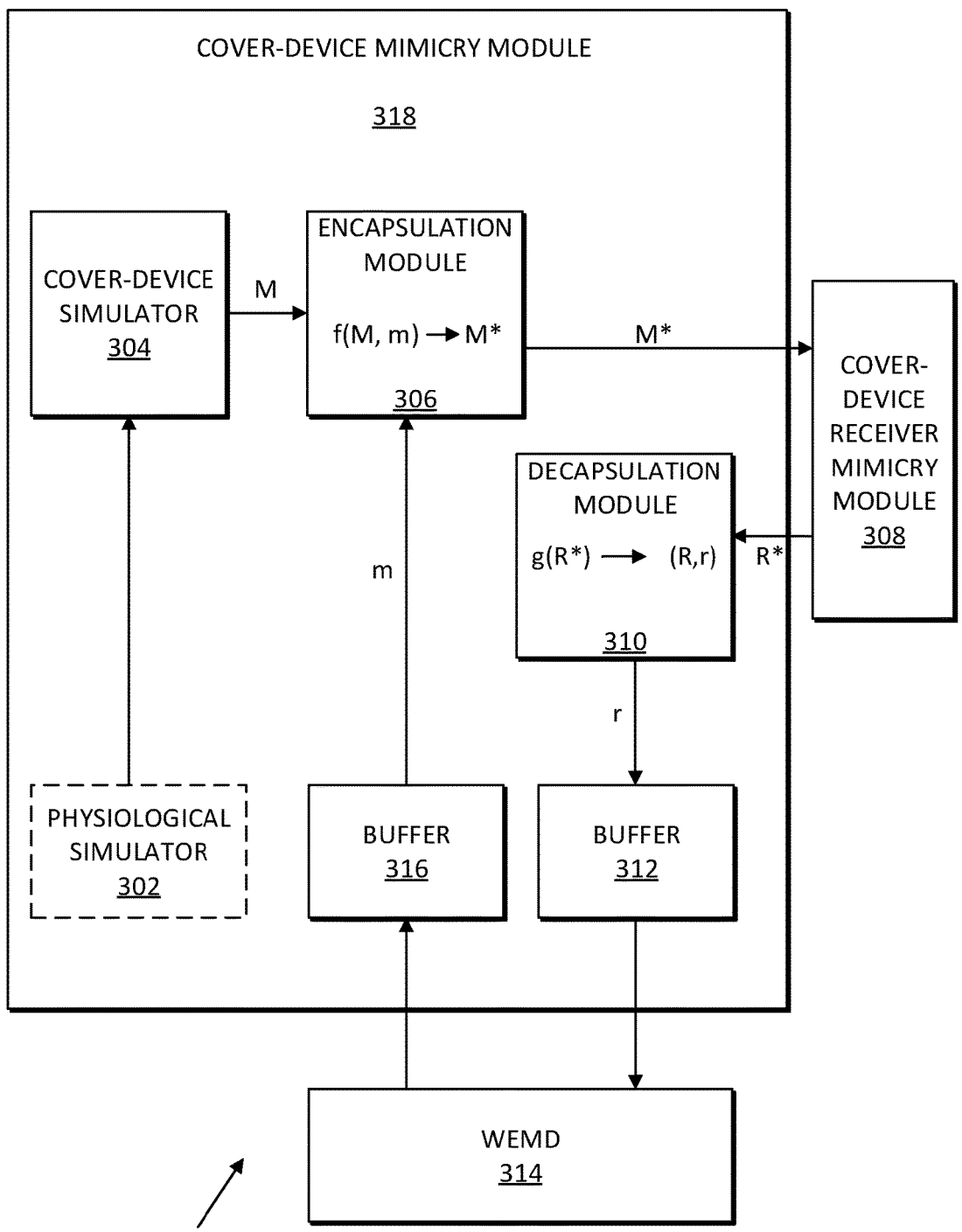
FIG. 3 is a functional block diagram of a WEMD with an exemplary cover-device mimicry module according to some embodiments. The exemplary mimicry module transmits traffic that appears to come from a cover device and receives traffic that appears to come from a cover receiver. The mimicry module embeds real WEMD traffic within cover traffic. The cover-receiver mimicry module is constructed analogously, but contains no physiological simulator.

FIG. 3 provides additional detail on an exemplary cover-device mimicry module 316. In the embodiment of FIG. 3, a physiological simulator 302 provides physiological values resembling those of the user. In simulating a selected cover device, real physiological parameter data may be buffered after reception from the WEMD 314. In another embodiment described below, physiological parameter measurements may be true measurements sent by a WEMD 314 or they may be derived from true physiological measurements sent by a WEMD 314. A cover device simulator 304 sends output M that resembles a cover device (e.g., simulated data is simulated heart rate data produced by a fitness device). Message M, for some embodiments, may encapsulate physiological parameter data in a message having a message type associated with a selected cover device type. For such embodiments, a WEMD 314 may be operative to encapsulate physiological parameter data in a message M having a message type associated with a selected cover device type. Alternatively, M may be a packet of special data, e.g., a null packet or other distinguished packet, designed to facilitate transmission of messages from a WEMD 314 at times when a cover device may not be transmitting. For example, in a safety zone, which is described in greater detail below, continuous traffic may be initiated through the sending of null packets by a cover-device simulator 304. In another embodiment, a selected cover device type is in a set of at least two selected cover device types, and wirelessly conveying physiological parameter data comprises multiplexing physiological parameter data across the at least two selected cover device types.

In some embodiments, simulating a selected cover device type may include sending a message using a packet length associated with a selected cover device type. Also, in some embodiments, simulating a selected cover device type includes sending a message using a packet timing associated with a selected cover device type.

As illustrated in FIG. 3, an encapsulation module 306 embeds m in M, yielding M*. This embedding may involve compression or removal of data in M or use of unused fields. M* is transmitted wirelessly to a cover-device receiver mimicry module 308. That module 308 performs decapsulation to extract a pair (M', m) from M*, where M' may include reconstructed or inferred elements removed from or compressed in M for the computation of M*.

As a mimicked cover device may not transmit data at a time when a message m is generated by a WEMD 314, a message m may be buffered. In this case, upon receiving a message M, an encapsulation module 306 may read a message m (or portion of m of a specified length) from a buffer 316. Similarly, if a WEMD 314 is not in a state such that the WEMD may receive a return message r from a decapsulation module 310 (e.g., if messages arrive in a burst at a rate higher than WEMD 314 is designed to receive), r may be buffered via buffer 312. Analogous buffers may be present in a WEMD-receiver.

The process for computation of R* proceeds analogously but without using physiological data. The cover-device receiver 308 may optionally communicate with a server to create complete end-to-end cover-traffic.

Modules for performing encryption and decryption are omitted from the illustration of FIG. 3. Some embodiments include modules to encrypt outgoing messages after their creation by the encapsulation module 306 and do so in a manner similar to the cover device. Similarly, incoming messages would be decrypted prior to the decapsulation module 310 receiving them.

Some embodiments perform physiologically-based cover-traffic synthesis. In such embodiments, a WEMD 314 may have access to data sources similar or identical to those of a cover device. A WEMD 314 may use these data sources as inputs to a physiological simulator 302. For example, a cardioverter defibrillator may supply pulse data for mimicry of a cover device, such as a fitness bracelet, that monitors pulse.

Some embodiments include an emergency-traffic override. In such embodiments, for certain WEMD 314 communications, timeliness may be a higher priority than privacy—for example, in a medical emergency. Embodiments disclosed herein include an override mechanism for such cases. Such a mechanism may be employed by a WEMD 314, or by a receiver. In one embodiment, the system determines whether a WEMD 314 is in an emergency override condition and ends simulation of a cover device in response to a determination that a WEMD 314 is in an emergency override condition.

In some embodiments, the system supports the designation of safety zones. In such embodiments, a WEMD 314 or receiver may detect that the user is in a location where the risk of eavesdropping is low and may transition to a higher-bandwidth or lower-power communication protocol without traffic-analysis protection. Additionally, the system may determine that a WEMD is in a predetermined safety zone and end cover device simulation in response to a determination that a WEMD is in a predetermined safety zone. For example, if a WEMD-receiver detects that a user is at home, a WEMD-receiver may deactivate the mimicry protocol.

Conversely, in some embodiments, the protective scheme proposed herein is normally inactive, but protective mimicry protocol is activated in response to a predetermined trigger or input. For example, the protocol may be initiated by an input from the user. In some embodiments, particular locations may be designated as high-risk zones. In response to a determination (made, for example, by a WEMD-receiver) that the user is in a high-risk zone, a mimicry protocol is initiated. For example, a WEMD-receiver may be provided with a GPS receiver and access to memory for storing information on high-risk zones. High-risk zones may include, for example, public locations such as shopping malls, places of business, office parks, and the user's particular place of business. A WEMD-receiver may use a mimicry protocol in response to other contextual cues as well. For example, in some embodiments, a WEMD-receiver determines the number of active W-Fi networks in range, with a higher density of Wi-Fi networks generally indicating a more public location and/or a location associated with business offices. A mimicry protocol is initiated in response to a determination that the number of Wi-Fi networks exceeds a threshold number, indicating a potential high-risk zone.

Some embodiments include features operative to address bandwidth limitations. While some embodiments choose a cover device that consumes more bandwidth and communicates at least as frequently as a WEMD 314, other embodiments use a cover-device channel with a lower bandwidth than a WEMD 314/receiver channel by multiplexing WEMD 314 communications over multiple cover devices or by buffering certain low-priority WEMD 314 and receiver messages and waiting until the user enters a safety zone.

In some embodiments, format-transforming encryption (FTE) is performed. If cover traffic is unencrypted, FTE may be used to create messages $M^*_1, M^*_2, \ldots$ to conceal the presence of an embedded channel.

In some embodiments, traffic shaping is performed. To protect against an adversary that does not analyze packet timings, only packet sizes and/or formats, some embodiments use a variant in which simulated cover device transmit packets similar to transmissions of a cover device only in size and/or syntax.

In some embodiments, protection against traffic analysis benefits from determination of a universal traffic profile. Rather than having a WEMD 314 mimic existing traffic patterns of cover devices, manufacturers of WEMDs 314 and cover devices might agree upon a universal traffic profile: a standard statistical profile for packet lengths and timings. Any type of device that adheres to such a protocol may be indistinguishable from any other such device type based on traffic analysis.

In an exemplary implementation, a user may be provided with an implantable cardioverter defibrillator (ICD) that is a WEMD 314. The presence of this device in a user's body may reveal to an eavesdropper that the user suffers from a medical condition such as cardiac arrhythmia. The presence of the device, in an especially hostile environment, may jeopardize a user's safety by exposing her medical device as a target for physical or cyber-attack.

An ICD may store an incremental log of cardiac measurements and therapeutic actions, with a mobile phone application ICD-App transmitting the measurements to a medical service provider. ICD data may be protected, for example, through mimicry of a fitness device FD that gathers data about a user's movements and pulse and periodically transmits a message M to a mobile phone application.

To provide such protection, a cover-device mimicry module 318 embeds a message m containing buffered log data from an ICD in a messageM, yielding messageM*. To send m within M*, an encapsulation module 306, for example, may send m in empty fields in FD packets. The encapsulation module 306 encrypts the messageM* and transmits M* to the cover-device receiver mimicry module 308. The cover-device receiver mimicry module 308 decapsulates m for use by the WEMD-receiver and produces a reconstruction M' of message M similar to a cover-device receiver.

As an ICD uses pulse data, an ICD may send such data to a physiological simulator 302. If an ICD contains an accelerometer, the ICD may send messages with gait information. Otherwise such information may be determined or simulated in a physiological simulator 302 based on the user's cardiac activity. An adversary eavesdropping on communications transmitted by this scheme may receive traffic that is difficult or impossible to distinguish from traffic transmitted by a true fitness device FD, making an ICD undetectable from transmission timings and contents.

Figure 4:
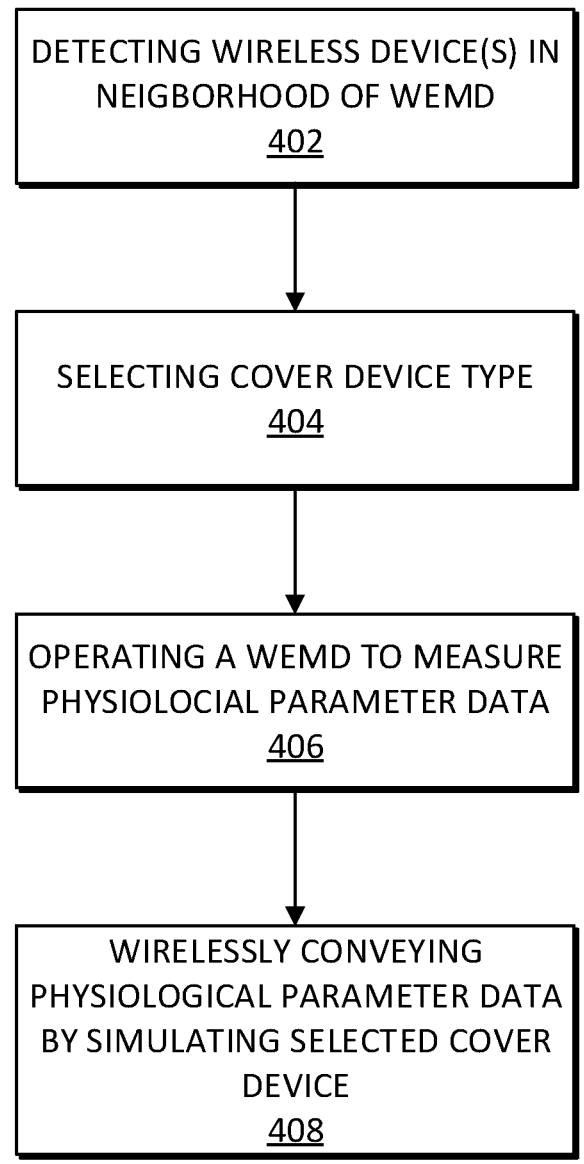
FIG. 4 is a flowchart for a method of concealing use of a wireless medical device (WEMD).

FIG. 4 shows an exemplary method 400 for concealing use of a wireless enabled medical device (WEMD). In step 402, wireless devices are detected within a neighborhood of a WEMD. This detection process 402 includes detecting device types for each detected wireless device. In one embodiment, a neighborhood comprises devices within transmission ranges for device protocols. Wi-Fi, for example, may have a range of 120-140 meters. Bluetooth, for example, may have a typical range of 100 m, 10 m, and 1 m for classes 1, 2, and 3, respectively. For one example embodiment, a device-setting module is operative to detect at least one device type of at least one respective wireless device in a neighborhood of a WEMD.

In step 404, a cover device type is selected. This selection process 404 is based at least in part on the at least one detected device type. In one embodiment, the cover device type selected may be selected so as to be different from at least one detected device type. The device-setting module is operative to select a cover device type so as to be different from the at least one detected device type. In one embodiment, when a detection process 402 and a cover device selection process 404 are performed by a receiver device, a selected cover device type may be transmitted from a receiver device to a WEMD. Selecting a cover device, for one embodiment, comprises displaying a list of detected device types to the user and receiving a user selection of a spurious detected device type that is not associated with a device carried by the user, where selection of a cover device type is based on, in part, a detected device type other than the spurious device type.

In a measurement process 406, a WEMD is operated to measure physiological parameter data. In the measurement process 406, the WEMD may simulate physiological data resembling data of the user (such as heart rate data produced by a fitness device). A wireless transmission process 408 wirelessly conveys physiological parameter data from a WEMD by simulating a selected cover device type. In one embodiment, simulating a selected cover device type comprises generating simulated data associated with a selected cover device type and transmitting the simulated data.

An exemplary method for conducting communications between a WEMD and a corresponding WEMD-receiver is described below. A cover device is used to conceal WEMD traffic. Selection may be made by the user, a WEMD, a WEMD-receiver, or a helper device (e.g., a mobile phone). Although selection may be performed by a WEMD, a WEMD-receiver, or a helper device, for clarity, the method is described as being performed by a WEMD-receiver.

A choice of cover device may be changed over time. A choice of cover device may be determined based on devices detected by a discovery protocol. If a WEMD or helper device determines that the user carries a true device identical or similar to a mimicked one, a different mimicked device choice may be made. A choice of cover device is communicated to both a WEMD and a receiver to enable sending of cover traffic at proper times.

After a cover device is selected, cover-traffic is generated. A cover-device simulator generates a message M In creating an embedded-channel, a message M has its data compressed or otherwise transformed, or unused fields in M are used to insert additional information in M without significant degradation to the fidelity of a cover-traffic simulation. For encapsulation, a message m originating with a WEMD is embedded in a transformed message M to create a message M*. A message M* is transmitted (in encrypted form) by a cover-device mimicry module to a cover-device receiver mimicry module. For decapsulation, a cover-device receiver mimicry module receives M* and extracts M', a reconstructed cover-device message, and m. Message M' is used in a cover-device receiver simulation process, and message m is sent to a WEMD-receiver. Traffic from a receiver to a WEMD is handled similarly via transmission from a cover-device receiver mimicry module to a cover-device mimicry module.

Figure 5:
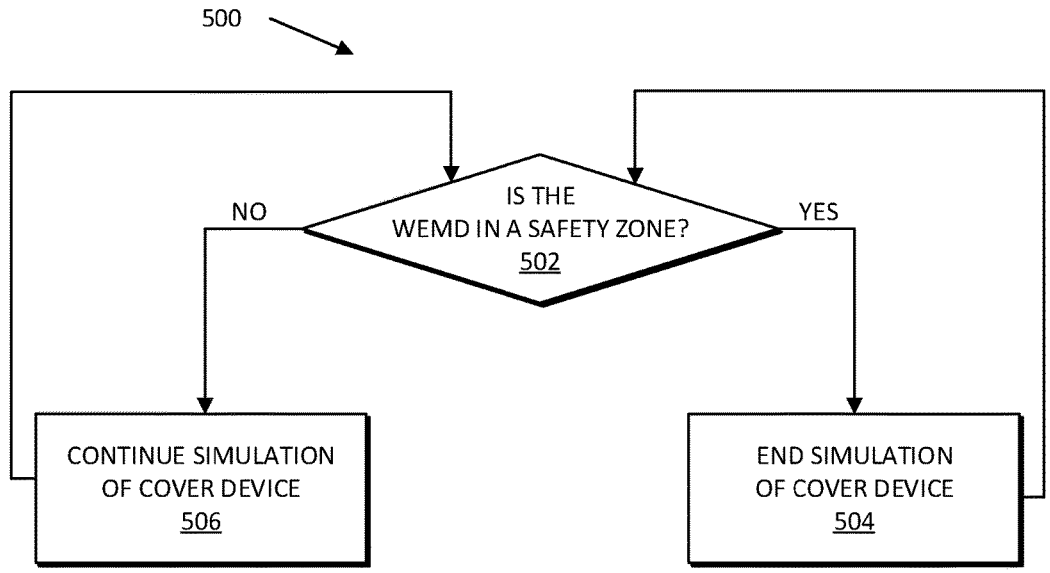
FIG. 5 is a flowchart for a method of determining if a WEMD is in a safety zone.

FIG. 5 is a flowchart of a method for determining whether a WEMD is in a safety zone. The safety zone process 500 starts with a decision process 502 that determines if the WEMD is in a safety zone. One embodiment checks to see if a condition flag has been set indicating a WEMD is in a safety zone. A safety zone condition flag may be set, for example, by receiving a broadcast message from an external device located in a medical facility. Another embodiment determines that the WEMD is in a safety zone based on a set of conditions, such as GPS coordinates corresponding to a safety zone or a lack of external detected devices. In another embodiment, a WEMD receives a message from a helper device, such as a smartphone, that indicates that the WEMD is in a safety zone. The helper device may receive input from the user indicating that the WEMD is in a safety zone. For example, when the user enters a house, a medical facility, or other safe area, the user may indicate this condition to a helper device, and a helper device may send a message to the WEMD with the user's safety zone indication. Once the WEMD determines that the WEMD is in a safety zone, a termination process 504 executes to end simulation of a cover device, and communications may be sent from the WEMD using a communication protocol that is native to that WEMD. If the WEMD is not in a safety zone, simulation of the cover device is continued in step 506.

Figure 6:
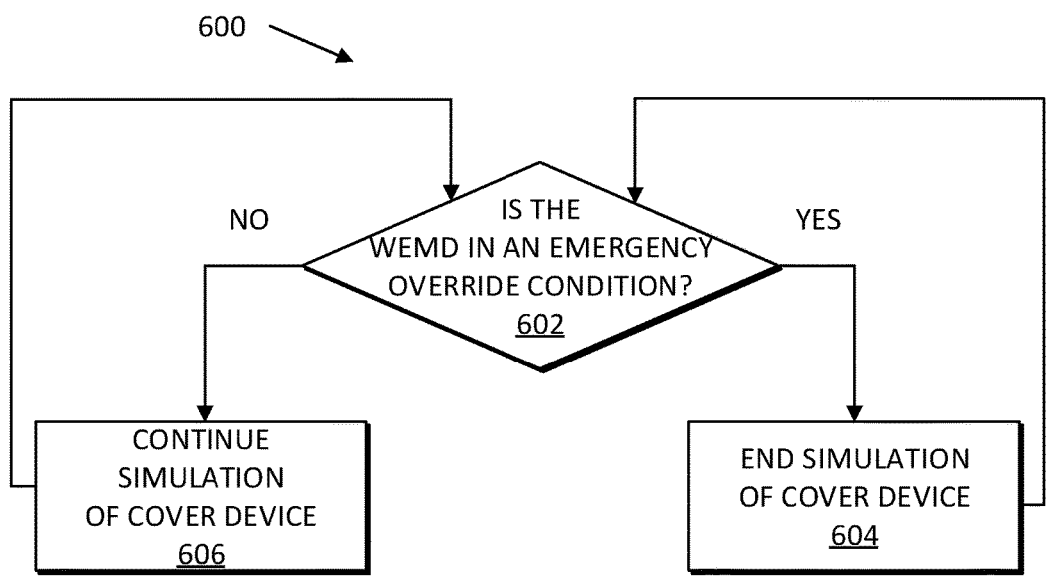
FIG. 6 is a flowchart for a method of determining if a WEMD is in an emergency override condition

FIG. 6 is a flowchart of a method for determining if a WEMD is in an emergency override condition. The emergency condition process 600 starts with a decision process 602 that determines if the WEMD is in an emergency override condition. One embodiment checks to see if a condition flag has been set indicating a WEMD is in an emergency override condition. An emergency override condition flag may be set, for example, by receiving a broadcast message from an external device, such as a device located in an ambulance. Another embodiment determines that the WEMD is in an emergency override condition based on a set of conditions, such as physiological measurements indicating a heart attack or other medical emergency. In another embodiment, a WEMD receives a message from a helper device, such as a smartphone, that indicates that the WEMD is in an emergency override condition. The helper device may receive input from the user indicating that the WEMD is in an emergency override condition. For example, when an emergency override condition occurs, the user may indicate this condition to a helper device, and a helper device may send a message to the WEMD with the user's emergency override condition indication. Once the WEMD determines that the WEMD is in an emergency override condition, a termination process 604 executes to end simulation of a cover device, and communications may be sent from the WEMD using a communication protocol that is native to that WEMD. If the WEMD is not in an emergency override condition, simulation of the cover device is continued in step 606.

Figure 7:
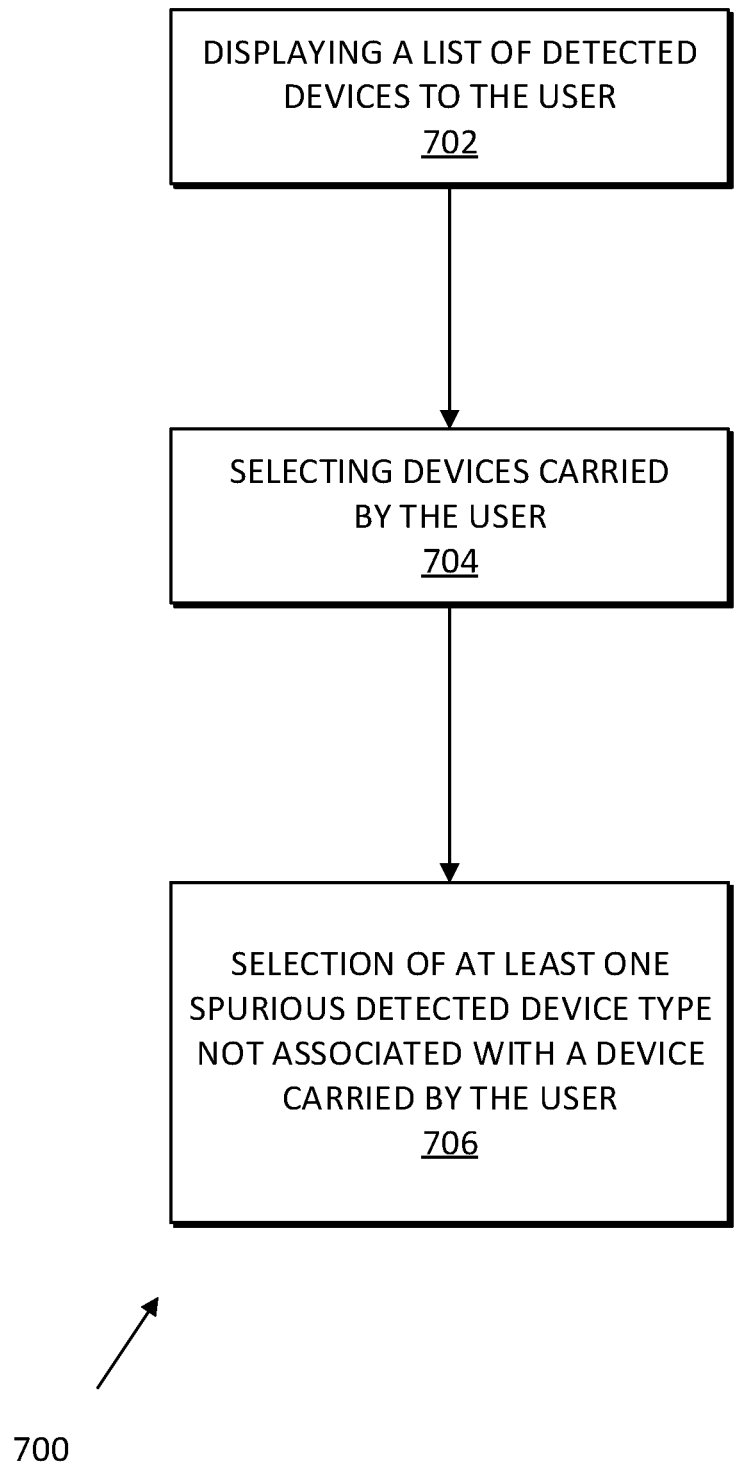
FIG. 7 is a flowchart for a method of selecting a cover device.

FIG. 7 is a functional block diagram of an example cover device selection method. In step 702, a list of detected devices is displayed to the user. The user, in step 704, may provide input indicating which, if any, of the detected devices is not being carried that user. For example, if a heartrate monitor is detected, but the user is not wearing a heartrate monitor, the user may indicate that the detected heartrate monitor is not associated with him (e.g., the detected heartrate monitor may belong to someone nearby). Conversely, in some embodiments, the user may identify which devices from among the detected devices are in fact being carried or worn by him. In a selection step 706, a cover device type is selected from among available device types that are not being carried or worn by that user. For example, if the user is wearing a heartrate monitor, a cover device type other than a heartrate monitor may be selected. (Otherwise, an eavesdropper who detects signals that appear to be from two different heartrate monitors on the same person may suspect the use of device mimicry.)

Embodiments disclosed herein may be layered on top of a WEMD or receiver with modifications made at the communication layer. Exemplary embodiments disclosed herein are implemented using wired and/or wireless network nodes, such as a wireless transmit/receive unit (WTRU) or other network entity. For example, a WEMD, WEMD-receiver, and/or helper device may be implemented by a WTRU as described herein with respect to FIG. 8.

Figure 8:
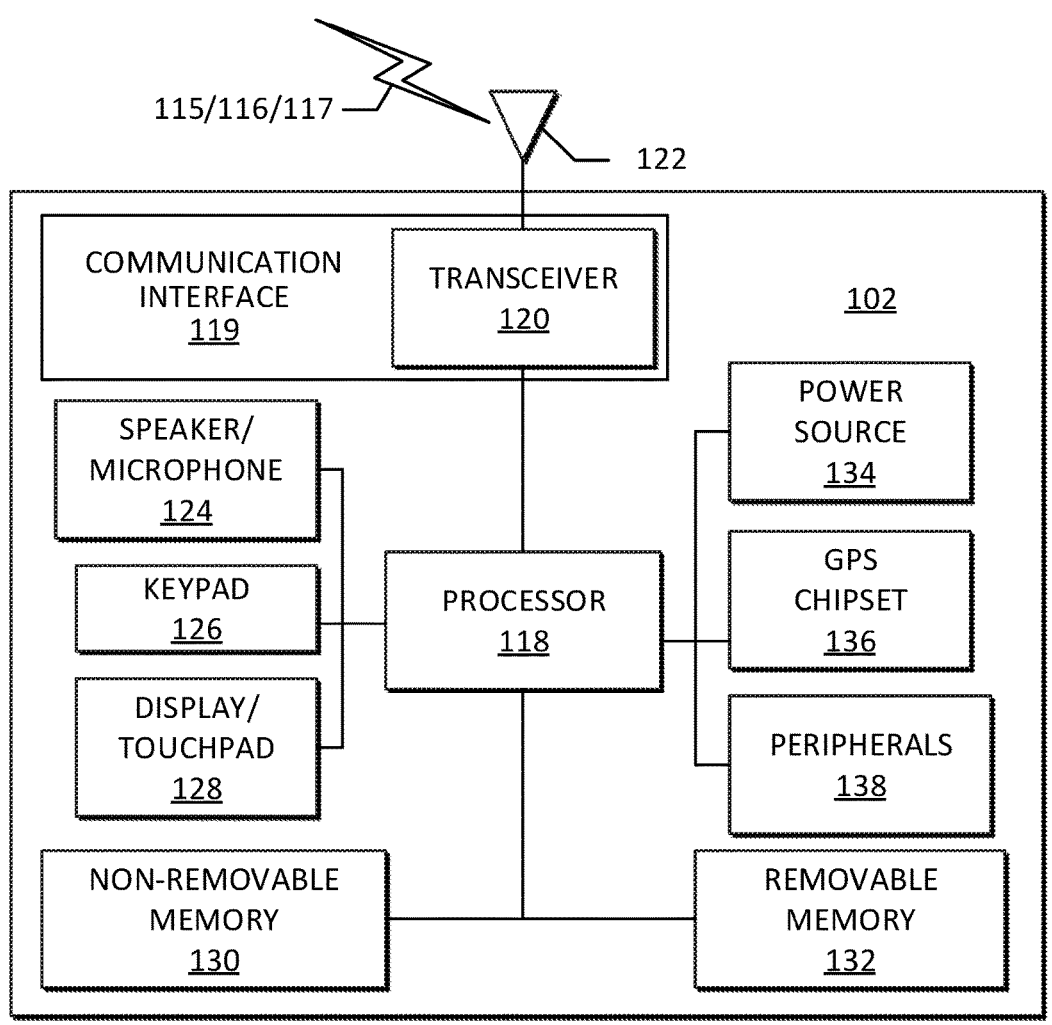
FIG. 8 is a functional block diagram of a wireless transmit-receive unit (WTRU) used in at least some embodiments disclosed herein.

FIG. 8 is a system diagram of an exemplary WTRU 102, which may be employed as a user device in embodiments described herein. As shown in FIG. 8, the WTRU 102 may include a processor 118, a communication interface 119 including a transceiver 120, a transmit/receive element 122, a speaker/microphone 124, a keypad 126, a display/touchpad 128, a non-removable memory 130, a removable memory 132, a power source 134, a global positioning system (GPS) chipset 136, and sensors 138. It will be appreciated that the WTRU 102 may include any sub-combination of the foregoing elements while remaining consistent with an embodiment.

The processor 118 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGAs) circuits, any other type of integrated circuit (IC), a state machine, and the like. The processor 118 may perform signal coding, data processing, power control, input/output processing, and/or any other functionality that enables the WTRU 102 to operate in a wireless environment. The processor 118 may be coupled to the transceiver 120, which may be coupled to the transmit/receive element 122. While FIG. 8 depicts the processor 118 and the transceiver 120 as separate components, it will be appreciated that the processor 118 and the transceiver 120 may be integrated together in an electronic package or chip.

The transmit/receive element 122 may be configured to transmit signals to, or receive signals from, a base station over the air interface 115/116/117. For example, in one embodiment, the transmit/receive element 122 may be an antenna configured to transmit and/or receive RF signals. In another embodiment, the transmit/receive element 122 may be an emitter/detector configured to transmit and/or receive IR, UV, or visible light signals, as examples. In yet another embodiment, the transmit/receive element 122 may be configured to transmit and receive both RF and light signals. It will be appreciated that the transmit/receive element 122 may be configured to transmit and/or receive any combination of wireless signals.

In addition, although the transmit/receive element 122 is depicted in FIG. 8 as a single element, the WTRU 102 may include any number of transmit/receive elements 122. More specifically, the WTRU 102 may employ MIMO technology. Thus, in one embodiment, the WTRU 102 may include two or more transmit/receive elements 122 (e.g., multiple antennas) for transmitting and receiving wireless signals over the air interface 115/116/117.

The transceiver 120 may be configured to modulate the signals that are to be transmitted by the transmit/receive element 122 and to demodulate the signals that are received by the transmit/receive element 122. As noted above, the WTRU 102 may have multi-mode capabilities. Thus, the transceiver 120 may include multiple transceivers for enabling the WTRU 102 to communicate via multiple RATs, such as UTRA and IEEE 802.11, as examples.

The processor 118 of the WTRU 102 may be coupled to, and may receive user input data from, the speaker/microphone 124, the keypad 126, and/or the display/touchpad 128 (e.g., a liquid crystal display (LCD) display unit or organic light-emitting diode (OLED) display unit). The processor 118 may also output user data to the speaker/microphone 124, the keypad 126, and/or the display/touchpad 128. In addition, the processor 118 may access information from, and store data in, any type of suitable memory, such as the non-removable memory 130 and/or the removable memory 132. The non-removable memory 130 may include random-access memory (RAM), read-only memory (ROM), a hard disk, or any other type of memory storage device. The removable memory 132 may include a subscriber identity module (SIM) card, a memory stick, a secure digital (SD) memory card, and the like. In other embodiments, the processor 118 may access information from, and store data in, memory that is not physically located on the WTRU 102, such as on a server or a home computer (not shown).

The processor 118 may receive power from the power source 134, and may be configured to distribute and/or control the power to the other components in the WTRU 102. The power source 134 may be any suitable device for powering the WTRU 102. As examples, the power source 134 may include one or more dry cell batteries (e.g., nickel-cadmium (NiCd), nickel-zinc (NiZn), nickel metal hydride (NiMH), lithium-ion (Li-ion), and the like), solar cells, fuel cells, and the like.

The processor 118 may also be coupled to the GPS chipset 136, which may be configured to provide location information (e.g., longitude and latitude) regarding the current location of the WTRU 102. In addition to, or in lieu of, the information from the GPS chipset 136, the WTRU 102 may receive location information over the air interface 115/116/117 from a base station and/or determine its location based on the timing of the signals being received from two or more nearby base stations. It will be appreciated that the WTRU 102 may acquire location information by way of any suitable location-determination method while remaining consistent with an embodiment.

The processor 118 may further be coupled to other peripherals 138, which may include one or more software and/or hardware modules that provide additional features, functionality and/or wired or wireless connectivity. For example, the peripherals 138 may include sensors such as an accelerometer, an e-compass, a satellite transceiver, a digital camera (for photographs or video), a universal serial bus (USB) port, a vibration device, a television transceiver, a hands free headset, a Bluetooth® module, a frequency modulated (FM) radio unit, a digital music player, a media player, a video game player module, an Internet browser, and the like.

It is also noted that, in this disclosure, various elements of one or more of the described embodiments are referred to as "modules" that carry out (i.e., perform, execute, and the like) various functions that are described herein in connection with the respective modules. As used herein, a module includes (or at least has access to) any necessary hardware (e.g., one or more processors, one or more microprocessors, one or more microcontrollers, one or more microchips, one or more application-specific integrated circuits (ASICs), one or more field programmable gate arrays (FPGAs), one or more memory devices, and/or one or more of any other type or types of devices and/or components) deemed suitable by those of skill in the relevant art for a given implementation. Each described module also includes (or at least has access to) any necessary instructions executable for carrying out the one or more functions described as being carried out by the respective module, and it is noted that those instructions may take the form of or include hardware (i.e., hardwired) instructions, firmware instructions, software instructions, and/or the like, and may be stored in any suitable non-transitory computer-readable medium or media.

Although features and elements are described above in particular combinations, one of ordinary skill in the art will appreciate that each feature or element may be used alone or in any combination with the other features and elements. In addition, the methods described herein may be implemented in a computer program, software, or firmware incorporated in a computer-readable medium for execution by a computer or processor. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

The invention claimed is:

1. A method of concealing use of a wireless-enabled medical device (WEMD), the method comprising:
   detecting at least one device type of at least one respective wireless device in a neighborhood of the WEMD;
   selecting a cover device type based at least in part on the at least one detected device type, wherein the cover device type is selected so as to be different from the at least one detected device type;

operating the WEMD to measure physiological parameter data; and wirelessly conveying the physiological parameter data from the WEMD by encapsulating the physiological parameter data in a message having a message type associated with the selected cover device type to simulate the selected cover device type.

2. The method of claim 1, wherein simulating the selected cover device type includes buffering the physiological parameter data prior to transmission from the WEMD.

3. The method of claim 1, wherein the detecting and the selecting are performed by a receiver device, further comprising transmitting the selected cover device type from the receiver device to the WEMD.

4. The method of claim 1, wherein simulating the selected cover device type includes sending a message using a packet length associated with the selected cover device type.

5. The method of claim 1, wherein simulating the selected cover device type includes sending a message using a packet timing associated with the selected cover device type.

6. The method of claim 1, further comprising:
determining whether the WEMD is in a predetermined safety zone; and
ending simulation in response to a determination that the WEMD is in the predetermined safety zone.

7. The method of claim 1, further comprising:
determining whether the WEMD is in an emergency override condition; and
ending simulation in response to a determination that the WEMD is in an emergency override condition.

8. The method of claim 1, wherein selecting a cover device comprises:
displaying a list of detected device types to the user; and
receiving user selection of at least one spurious detected device type that is not associated with a device carried by the user;
wherein the selection of the cover device type is based at least in part on the detected device types other than the spurious device type.

9. The method of claim 1, wherein simulating the selected cover device type comprises:

generating simulated data associated with the selected cover device type; and
transmitting the simulated data.

10. The method of claim 9, wherein the simulated data is simulated heart rate data.

11. The method of claim 1, wherein the WEMD is an implantable cardioverter defibrillator (ICD).

12. The method of claim 1, wherein the selected cover device type is in a set of at least two selected cover device types, and wherein wirelessly conveying the physiological parameter data comprises multiplexing the physiological parameter data across the at least two selected cover device types.

13. The method of claim 1, wherein the cover device type is selected from a predetermined list of available cover device types.

14. The method of claim 13, further comprising calculating a utility function for a plurality of the available cover device types, wherein the selection of the cover device type is based on at least in part on the calculated utility function.

15. A wireless enabled medical device (WEMD) system comprising:
a device-setting module operative to detect at least one device type of at least one respective wireless device in a neighborhood of the WEMD and to select a cover device type based at least in part on the at least one detected device type, wherein the device-setting module is operative to select the cover device type so as to be different from the at least one detected device type; and
a WEMD operative to measure physiological parameter data and to wirelessly convey the physiological parameter data from the WEMD, wherein the WEMD is operative to encapsulate the physiological parameter data in a message having a message type associated with the selected cover device type to simulate the selected cover device type.

16. The system of claim 15, further comprising a receiver device, wherein the device-setting module is included in the receiver device.

* * * * *